United States Patent
Ito et al.

(10) Patent No.: US 12,258,364 B2
(45) Date of Patent: Mar. 25, 2025

(54) METHOD FOR PURIFYING PHOSPHORUS-CONTAINING OLEFIN COMPOUND SALT AND METHOD FOR PRODUCING OLEFIN COMPOUND USING PURIFIED PRODUCT OBTAINED THEREBY

(71) Applicant: DAIKIN INDUSTRIES, LTD., Osaka (JP)

(72) Inventors: Yuuko Ito, Osaka (JP); Tsubasa Nakaue, Osaka (JP); Takehiro Chaki, Osaka (JP); Takashi Usui, Osaka (JP); Tomoyuki Iwamoto, Osaka (JP); Megumi Kushida, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 402 days.

(21) Appl. No.: 17/584,818

(22) Filed: Jan. 26, 2022

(65) Prior Publication Data
US 2022/0144864 A1  May 12, 2022

Related U.S. Application Data

(63) Continuation of application No. PCT/JP2020/029796, filed on Aug. 4, 2020.

(30) Foreign Application Priority Data

Aug. 6, 2019  (JP) .................................. 2019-144223

(51) Int. Cl.
C07F 9/52 (2006.01)
C07C 17/354 (2006.01)

(52) U.S. Cl.
CPC .............. *C07F 9/52* (2013.01); *C07C 17/354* (2013.01)

(58) Field of Classification Search
CPC ........ C07F 9/52; C07F 9/5304; C07F 9/5428; C07F 9/5013; C07F 9/5095; C07C 17/354; C07C 17/35
See application file for complete search history.

(56) References Cited

FOREIGN PATENT DOCUMENTS

EP      4 011 855       6/2022

OTHER PUBLICATIONS

Ov Akimy An, M.Z. et al. Halogenation of quaternary phosphonium salts containing prop-1 (2)-enyl group. Russian Journal of General Chemistry. 2017, vol. 87, No. 8, pp. 1727-1730. (Year: 2017).*
Rabinowitz, R. et al. Synthesis of vinylphosphonium compounds. Journal of Polymer Science, Part A. 1965, vol. 3, No. 5, pp. 2055-2061. (Year: 1965).*
Frohn, H. et al. The unusual reactivity of C3F7OCF=CF2 with PBu3 and the complex hydrides M[EH4] (M: Li, Na; E: B, Al); preparation of potassium perfluoro-2-propoxyeth-1-enyltrifluoroborate K[C3F7OCF=CFBF3]. Journal of Fluorine Chemistry. 2003, vol. 123, pp. 43-49 (Year: 2003).*
Burton, D.J. et al. Preparation of E-1,2,3,3,3-pentafluoropropene, Z-1,2,3,3,3-pentafluoropropene and E-1-iodopentafluoropropene. Journal of Fluorine Chemistry. 1989, vol. 44, No. 1, pp. 167-174 (Year: 1989).*

(Continued)

*Primary Examiner* — Deborah D Carr
(74) *Attorney, Agent, or Firm* — Wenderoth, Lind & Ponack, L.L.P.

(57) ABSTRACT

Provided is a method for purifying a phosphorus-containing olefin compound salt as a raw material or an intermediate that is useful to increase the purity of a target product in a method for producing an olefin compound and that can be applied to the production method, and a method for producing an olefin compound using a purified product obtained thereby.

Specifically, provided is a method for purifying a phosphorus-containing olefin compound salt, comprising reprecipitating and/or recrystallizing a solid comprising at least one phosphorus-containing olefin compound salt selected from the group consisting of:

a phosphorus-containing olefin compound salt A represented by the following formula (1):

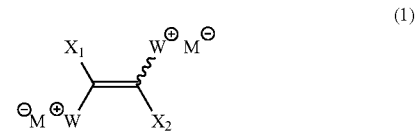

(1)

wherein $X_1$ and $X_2$ are each independently F, Cl, Br, I, or H; $W^+$s are the same or different and each is a monovalent cation comprising $PR_3$ or $P(OR)_3$, provided that Rs are groups having a saturated or unsaturated structure containing C and H, are optionally bonded together to form a ring, and optionally contain an atom other than C and H; three Rs included in $R_3$ and $(OR)_3$ are optionally the same or different; and $M^-$ is a monovalent anion comprising an atom or a compound; and a phosphorus-containing olefin compound salt B represented by the following formula (2):

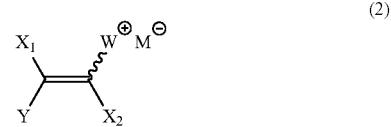

(2)

wherein $X_1$, $X_2$, $W^+$, and $M^-$ are as defined above, and Y is F, Cl, Br, I, H, an alkyl group, an alkyl ether group, a fluoroalkyl group, or a fluoroalkyl ether group;
in a solvent, thereby obtaining a purified product of the phosphorus-containing olefin compound salt.

9 Claims, No Drawings

(56) References Cited

OTHER PUBLICATIONS

Frohn, H.J. et al. (Fluoroorgano)fluoroboranes and -fluoroborates. 2. Synthesis and spectroscopic characterization of potassium polyfluoroalken-1-yltrifluoroborates. Zeitschrift fuer Anorganische und Allgemeine Chemie. 2001, vol. 627, No. 11, pp. 2499-2505 (Year: 2001).*

International Search Report issued Sep. 24, 2020 in International (PCT) Application No. PCT/JP2020/029796.

Ovakimyan et al., "Halogenation of Quaternary Phosphonium Salts Containing Prop-l(2)-enyl Group", Russian Journal of General Chemistry, vol. 87, No. 8, 2017, pp. 1727-1730.

Maier et al., "Vinyl Derivatives of the Metals. VI. Preparation, Properties and Some Reactions of Trivinyl Compounds of Group V Elements", Journal of the American Chemical Society, vol. 79, 1957, pp. 5884-5889.

Rabinowitz et al., "Synthesis of Vinylphosphonium Compounds", Journal of Polymer Science, vol. 3, No. 5, 1965, pp. 2055-2061.

Burton et al., "Fluorine Chemistry Synthesis", Journal of Fluorine Chemistry, vol. 44, 1989, pp. 167-174.

Frohn et al., "(Fluoroorgano)fluoroboranes and -fluoroborates. Synthesis of Spectroscopic Characterization of Potassium Polyfluoroalken-1-yltrifluoroborates", Zeitschrift fuer Anorganische und Allgemeine Chemie, vol. 627, No. 11, 2001, pp. 2499-2505.

Frohn et al., "The unusual reactivity of $C_3F_7OCF=CF_2$ with $PB_{u3}$ and the complex hydrides $M[EH_4]$ (M: Li, Na; E: B, Al);. Preparation of potassium perfluoro-2-propoxyeth-1-enyltrifluoroborate $K[C_3F_7OCF=CFBF_3]$", Journal of Fluorine Chemistry, vol. 123, 2003, pp. 43-49.

Extended European Search Report issued Jun. 28, 2023 in corresponding European Patent Application No. 20850570.1.

R. Blachnik et al., "Crystal structure of 1,2-vinylen-bis(triphenylphosphonium) bis(boron tetrafluoride), $[Ph_3P—CH=CH—PPh_3][BF_4]_2$", Z. Kristallogr. New Crystal Structres, vol. 2016, No. 1-4, (Apr. 1, 2001), pp. 209-210.

H. Wessolowski et al., "Novel perfluoroalkenylphosphonates and iodoperfluoroalkenes from 3, 3-bis (trifluoromethyl)-1,1,2,4,4,4-hexafluoro-1-butylene and nonafluoro-n-butoxy-1, 1, 2-trifluoroethylene", Journal of Fluorine Chemistry, vol. 80, (Oct. 1, 1996), pp. 149-152.

* cited by examiner

METHOD FOR PURIFYING PHOSPHORUS-CONTAINING OLEFIN COMPOUND SALT AND METHOD FOR PRODUCING OLEFIN COMPOUND USING PURIFIED PRODUCT OBTAINED THEREBY

TECHNICAL FIELD

The present disclosure relates to a method for purifying a phosphorus-containing olefin compound salt and a method for producing an olefin compound using a purified product obtained thereby.

BACKGROUND ART (E)-1,2-difluoroethylene (hereinafter referred to as "R1132(E)") has a low global warming potential (GWP), and thus has attracted attention as an alternative refrigerant to difluoromethane (R-32) and 1,1,1,2,2-pentafluoroethane (R-125), which are greenhouse gases.

Conventionally, as a method for producing R1132(E), for example, NPL 1 has reported that a reaction product containing a target product can be obtained according to the following procedure (Abstract and "3.2. Reactions of olefin 1 with Pbu3," in particular, 3.2.2).

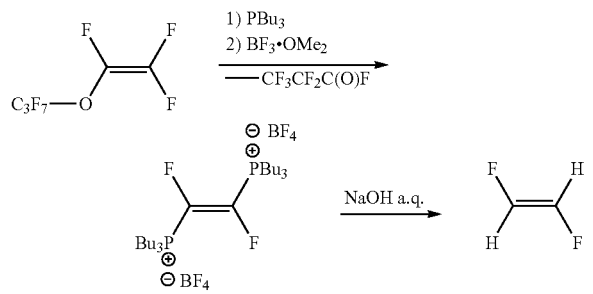

The above report example states that in addition to the target product R1132(E), about 16% (0.3 g for 1.9 g) of cis- and trans-1H-nonafluoro-2-propoxyethene (cis:trans=1:5) was also present as an impurity.

CITATION LIST

Non-Patent Literature

NPL 1: Journal of Fluorine Chemistry, 123 (2003) 43-49

SUMMARY

A method for purifying a phosphorus-containing olefin compound salt, comprising reprecipitating and/or recrystallizing a solid comprising at least one phosphorus-containing olefin compound salt selected from the group consisting of:

a phosphorus-containing olefin compound salt A represented by the following formula (1):

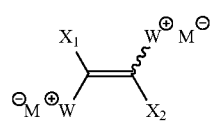

(1)

wherein $X_1$ and $X_2$ are each independently F, Cl, Br, I, or H; $W^+$s are the same or different and each is a monovalent cation comprising $PR_3$ or $P(OR)_3$, provided that Rs are groups having a saturated or unsaturated structure containing C and H, are optionally bonded together to form a ring, and optionally contain an atom other than C and H; three Rs included in $R_3$ and $(OR)_3$ are optionally the same or different; and $M^-$ is a monovalent anion comprising an atom or a compound; and a phosphorus-containing olefin compound salt B represented by the following formula (2):

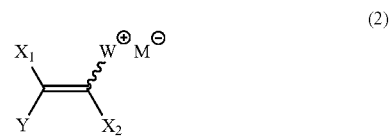

(2)

wherein $X_1$, $X_2$, $W^+$, and $M^-$ are as defined above, and Y is F, Cl, Br, I, H, an alkyl group, an alkyl ether group, a fluoroalkyl group, or a fluoroalkyl ether group;

in a solvent, thereby obtaining a purified product of the phosphorus-containing olefin compound salt.

Advantageous Effects

According to the method for purifying a phosphorus-containing olefin compound salt of the present disclosure, a solid containing the salt is reprecipitated and/or recrystallized in a solvent, thereby obtaining a highly purified product of the phosphorus-containing olefin compound salt. The purified product of the phosphorus-containing olefin compound salt is useful as a raw material or an intermediate in a method for producing an olefin compound. An olefin compound with high purity can be produced by synthesizing the target product using the purified product as a raw material or an intermediate.

DESCRIPTION OF EMBODIMENTS

The method for purifying a phosphorus-containing olefin compound salt of the present disclosure comprises reprecipitating and/or recrystallizing a solid comprising at least one phosphorus-containing olefin compound salt selected from the group consisting of:

a phosphorus-containing olefin compound salt A represented by the following formula (1):

(1)

wherein $X_1$ and $X_2$ are each independently F, Cl, Br, I, or H; $W^+$s are the same or different and each is a monovalent cation comprising $PR_3$ or $P(OR)_3$, provided that Rs are groups having a saturated or unsaturated structure containing C and H, are optionally bonded together to form a ring, and optionally contain an atom other than C and H; three Rs included in $R_3$ and $(OR)_3$ are optionally the same or different; and $M^-$ is a monovalent anion comprising an atom or a compound; and a phosphorus-containing olefin compound salt B represented by the following formula (2):

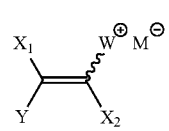

(2)

wherein $X_1$, $X_2$, $W^+$, and $M^-$ are as defined above, and Y is F, Cl, Br, I, H, an alkyl group, an alkyl ether group, a fluoroalkyl group, or a fluoroalkyl ether group;
in a solvent, thereby obtaining a purified product of the phosphorus-containing olefin compound salt.

According to the method for purifying a phosphorus-containing olefin compound salt of the present disclosure, which has the above feature, a solid containing the salt is reprecipitated and/or recrystallized in a solvent, thereby obtaining a highly purified product of the phosphorus-containing olefin compound salt. Such a purified product of the phosphorus-containing olefin compound salt is useful as a raw material or an intermediate in a method for producing an olefin compound. An olefin compound with high purity can be produced by synthesizing the target product using the purified product as a raw material or an intermediate.

The phosphorus-containing olefin compound salt A is represented by the following formula (1):

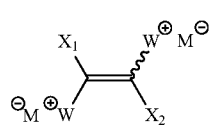

(1)

wherein $X_1$ and $X_2$ are each independently F, Cl, Br, I, or H; $W^+$s are the same or different and each is a monovalent cation comprising $PR_3$ or $P(OR)_3$, provided that Rs are groups having a saturated or unsaturated structure containing C and H, are optionally bonded together to form a ring, and optionally contain an atom other than C and H; three Rs included in R3 and $(OR)_3$ are optionally the same or different; and $M^-$ is a monovalent anion comprising an atom or a compound.

$X_1$ and $X_3$ are each independently F, Cl, Br, I, or H. Of these, when the purified product is used as a raw material or an intermediate in a method for producing an olefin compound, and when the target olefin compound is R1132(E), $X_1$ and $X_2$ are both preferably F.

$W^+$s are the same or different and each is a monovalent cation comprising $PR_3$ or $P(OR)_3$, provided that Rs are groups having a saturated or unsaturated structure containing C and H, are optionally bonded together to form a ring, and optionally contain an atom other than C and H. That is, $W^+$s are cations of organic phosphine compounds.

Rs are groups having a saturated or unsaturated structure containing C and H, are optionally bonded together to form a ring, and optionally contain an atom other than C and H. Examples of a hydrocarbon group, which is a kind of the skeleton of this group, include alkyl, alkenyl, alkynyl, aryl, arylalkyl, and arylalkenyl groups, as well as hydrocarbon groups having a double or triple bond that satisfy the above requirements. These hydrocarbon groups may be bonded together to form a ring, and may have a substituent containing an atom other than C and H.

The number of carbon atoms in the above alkyl group, alkenyl group, and alkynyl group (hereinafter collectively referred to as the "alkyl group etc.") is not limited. The number of carbon atoms in the alkyl group is preferably 1 to 10, more preferably 1 to 8, even more preferably 1 to 6, and most preferably 1 to 4. Further, the number of carbon atoms in the alkenyl group and alkynyl group is preferably 2 to 10, more preferably 2 to 8, even more preferably 2 to 6, and most preferably 2 to 4. When the alkyl group etc. have a cyclic structure, the number of carbon atoms is preferably 4 to 12, more preferably 4 to 10, even more preferably 5 to 8, and most preferably 6 to 8.

The structure of the alkyl group etc. is not limited as long as the above requirements of Rs are satisfied. The alkyl group etc. may be linear or may have a side chain. The alkyl group etc. may have a chain structure or a cyclic structure (cycloalkyl group, cycloalkenyl group, or cycloalkynyl group). The alkyl group etc. may also have one or two or more substituents containing an atom other than C and H. In addition to such substituents, the alkyl group etc. may contain one or two or more atoms other than C and H in the chain structure or the cyclic structure. Examples of atoms other than C and H include one or two more of O, N, and S.

Examples of the alkyl group include methyl, ethyl, n-propyl, i-propyl, n-butyl, i-butyl, sec-butyl, t-butyl, pentyl, isopentyl, neopentyl, hexyl, heptyl, octyl, and 2-ethylhexyl groups. Examples of the cycloalkyl group include cyclopentyl, cyclohexyl, cycloheptyl, and 2-methylcyclohexyl groups. Examples of the alkenyl group include vinyl, allyl, and isopropenyl groups. Examples of the cycloalkenyl group include a cyclohexenyl group.

The number of carbon atoms in the above aryl group, arylalkyl group, and arylalkenyl group (hereinafter collectively referred to as the "aryl group etc.") is not limited. The number of carbon atoms is preferably 6 to 15, more preferably 6 to 12, and even more preferably 6 to 10.

The structure of the aryl group etc. is not limited as long as the above requirements of Rs are satisfied. The aryl group etc. may have one or two or more substituents. For example, the aromatic ring contained in the aryl group etc. may have one or two or more substituents. The position of the substituents may be any of o-, m-, and p-. Examples of the substituents include one or two or more of halogen atoms (e.g., fluorine, chlorine, and bromine atoms), alkyl groups, alkenyl groups, nitro groups, amino groups, hydroxyl groups, and alkoxy groups. When such a substituent is located on the aromatic ring, the position of the substituent may be any of o-, m-, and p-.

Examples of the aryl group include phenyl, tolyl, ethylphenyl, xylyl, cumenyl, mesityl, methoxyphenyl (o-, m-, and p-), ethoxyphenyl (o-, m-, and p-), 1-naphthyl, 2-naphthyl, and biphenylyl groups. Examples of the arylalkyl group include benzyl, methoxybenzyl (o-, m-, and p-), ethoxybenzyl (o-, m-, and p-), and phenethyl groups. Examples of the arylalkenyl group include styryl and cinnamyl groups.

Three Rs included in $PR_3$ and $P(OR)_3$ may be bonded together to form a ring. The structure of the ring is not limited. For example, the number of ring members can generally be 4 to 10, and preferably 5 to 8, including a phosphorus atom. The number of ring members is generally 5 or 6. The ring may contain heteroatoms (e.g., oxygen, nitrogen, and sulfur atoms) in its structure. Further, the ring may have other substituents. The ring may also have an unsaturated bond in its structure.

Three Rs included in $PR_3$ and $P(OR)_3$ may have the same or different structures.

$M^-$ is a monovalent anion comprising an atom or a compound.

Examples of the atom or compound that forms the anion include halogen ions, such as fluorine, chlorine, bromine, and iodine; carboxyl ions, such as formic acid, acetic acid, and oxalic acid; sulfonate ions, such as methanesulfonyloxy, trifluoromethanesulfonyloxy, benzenesulfonyloxy, and toluenesulfonyloxy; antimony fluoride ions; phosphorus fluoride ions; arsenic fluoride ions; boron fluoride ions; perchlorate ions; and the like. Of these, when the purified product is used as a raw material or an intermediate in a method for producing an olefin compound, and when the target olefin compound is R1132(E), boron fluoride ions are preferred.

The phosphorus-containing olefin compound salt B is represented by the following formula (2):

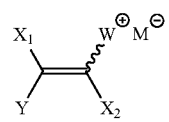

(2)

wherein $X_1$, $X_2$, $W^+$s, and $M^-$ are as defined above, and Y is F, Cl, Br, I, H, an alkyl group, an alkyl ether group, a fluoroalkyl group, or a fluoroalkyl ether group.

The explanations of $X_1$, $X_2$, $W^+$s, and $M^-$ are the same as those for the phosphorus-containing olefin compound salt A.

Y is F, Cl, Br, I, H, an alkyl group, an alkyl ether group, a fluoroalkyl group, or a fluoroalkyl ether group.

The explanation of the alkyl group is the same as that of Rs (alkyl groups) in the phosphorus-containing olefin compound salt A.

Examples of the alkyl ether group include compounds with oxygen atoms bonded to Rs (alkyl groups) in the phosphorus-containing olefin compound salt A.

Examples of the fluoroalkyl group include compounds with fluorine atoms substituted on carbon atoms in any number and in any combination. Of these, preferred are $C_{1-4}$ compounds, and particularly preferred are $C_1$ compounds.

Examples of the fluoroalkyl ether group include compounds with an oxygen atom bonded to the fluoroalkyl group.

The method for purifying a phosphorus-containing olefin compound salt of the present disclosure comprises reprecipitating and/or recrystallizing a solid containing at least one of the phosphorus-containing olefin compound salt A and the phosphorus-containing olefin compound salt B in a solvent, thereby obtaining a purified product of the phosphorus-containing olefin compound salt. A part or whole of the phosphorus-containing olefin compound salt may be a crystal. In the present disclosure, considering that the salt may partially contain non-crystalline portions and that the salt contains impurities (expressed as "compound" in the claims), the whole, including the salt and impurities, is described as a "solid." Further, in identifying the purification method, the method is described as "reprecipitation and/or recrystallization" so that the method is not limited to recrystallization alone for the above reason.

The solid is not limited as long as there is room to reduce the amount of impurities contained in the solid by reprecipitation and/or recrystallization to increase purity. The amount of impurities contained in the solid to be reprecipitated and/or recrystallized is not limited, but is about 5 to 70 mass %, for example.

The solid containing at least one of the phosphorus-containing olefin compound salt A and the phosphorus-containing olefin compound salt B is not limited. When the solid is applied to a method for producing an olefin compound by reacting the purified product with a base to perform dephosphorization and hydrogenation, thereby obtaining an olefin compound, the solid preferably contains a phosphorus-containing olefin compound salt as a production raw material or intermediate of the target olefin compound.

For example, in the production process of R1132(E) as shown below:

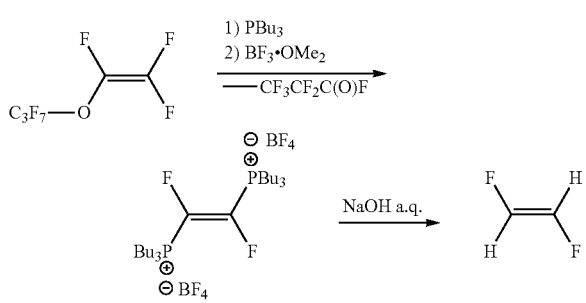

the phosphorus-containing olefin compound salt to be reacted with the base is one of the specific examples of the phosphorus-containing olefin compound salt A in the present disclosure. For example, in the production process of R1132 (E), the solid containing a phosphorus-containing olefin compound salt contains at least one compound (impurity) selected from the group consisting of:

(trans-2-perfluoropropoxy-1,2-difluoroethen-1-yl) (tributyl) phosphonium tetrafluoroboranuide,
[trans-$C_3F_7OCF$=$CFPBu_3$][$BF_4$],
(cis-2-perfluoropropoxy-1,2-difluoroethen-1-yl)(tributyl) phosphonium tetrafluoroboranuide,
[cis-$C_3F_7OCF$=$CFPBu_3$][$BF_4$],
perfluoropropoxy vinyl ether ($C_3VE$),
(2,2,3,3,3-pentafluoro-1-tributylphosphin-1-one) tetrafluoroboranuide ([$CF_3CF_2C(O)$—$PBu_3$][$BF_4$]),
boron trifluoride tributylphosphine oxide ($BF_3 \cdot O$=$PBu_3$),
tetrafluoroboric acid ($HBF_4$),
(1,2-difluoroethen-1-yl)(tributyl) phosphonium tetrafluoroboranuide) ([$CHF$=$CFPBu_3$][$BF_4$]),
diethyl ether ($Et_2O$),
dimethyl ether ($Mt_2O$), and
2-methoxy-2-methylpropane (MTBE).

Although the conditions for reprecipitation and/or recrystallization are not limited, the solvent is preferably, for example, at least one member selected from the group consisting of ethyl acetate, n-propyl acetate, isopropyl acetate, n-butyl acetate, methanol, ethanol, propanol, isopropanol, and butanol. Of these, ethyl acetate is more preferred in terms of the solubility of the solid and the cost of the solvent. The pH during reprecipitation and/or recrystallization is preferably 8 or less. By setting the pH in such a range, hydrolysis of the phosphorus-containing olefin compound salt can be prevented, and reprecipitation and/or recrystallization can be performed. The number of times of reprecipitation and/or recrystallization is not limited; however, in the purification method of the present disclosure, in particular, when the following suitable conditions are used, it is possible to obtain a purified product with high purity (95 mass % or more) by one treatment.

The temperature at which the solid is dissolved in a solvent, and the conditions for reducing the temperature of the solution after that are not limited. In tams of solubility, a solvent at 45 to 60° C. is preferred. It is preferable that after dissolution in such a solvent, the temperature of the solution is reduced at −0.25° C./min or less to perform reprecipitation and/or recrystallization. It is more preferable that after dissolution in a solvent at 45 to 50° C., the temperature of the solution is reduced at −0.25° C./min or less to perform reprecipitation and/or recrystallization. −0.20° C./min or less is more preferred, and −0.15° C./min or less is even more preferred. In terms of obtaining a purified product with high purity, it is preferable to slowly reduce the temperature of the solution as described above.

The method for extracting the purified product is not limited. For example, it is preferable that the purification method of the present disclosure further has a step of extracting the purified product by suction filtration and/or pressure filtration. In doing so, it is more preferable that the temperature of the mixture containing the purified product is 5° C. or lower.

According to the purification method of the present disclosure, at least some of the impurities are removed by reprecipitation and/or recrystallization. Therefore, the purity of the phosphorus-containing olefin compound salt in the purified product is preferably 95 mass % or more, and more preferably 99 mass % or more.

The purified product (phosphorus-containing olefin compound salt) with impurities that are reduced in this way can be applied to, for example, a method for producing an olefin compound by reacting the purified product with a base to perform dephosphorization and hydrogenation, thereby obtaining an olefin compound. In this case, since the purity of the phosphorus-containing olefin compound salt is improved in the purified product, the target olefin compound can be synthesized with high purity. In particular, the phosphorus-containing olefin compound salt in the production method of R1132(E) disclosed in NPL 1 described in the background art section is not purified as in the present disclosure. Together with R1132(E), which is the target compound, low-boiling-point components, such as 1,1,2-trifluoroethylene, pentafluoroethane (R-125), R-134a, and (Z)-1,2-difluoroethylene (R1132(Z)), which are difficult to separate by distillation, are produced as by-products; however, the production of these low-boiling-point components as by-products can be suppressed by using the purified product after the purification method of the present disclosure to produce an olefin compound. In this respect, the present disclosure is more highly useful than the prior art.

That is, the present disclosure includes a method for producing an olefin compound, comprising reacting a purified product of at least one phosphorus-containing olefin compound salt selected from the group consisting of the phosphorus-containing olefin compound salt A and the phosphorus-containing olefin compound salt B obtained by the purification method of the present disclosure with a base to obtain a reaction product containing a dephosphorized and hydrogenated olefin compound. In the present disclosure, the target olefin compound is preferably, for example, (E)-1,2-difluoroethylene (R1132(E)).

The reaction product in the method for producing an olefin compound of the present disclosure contains (E)-1,2-difluoroethylene and, for example, at least one member selected from the group consisting of acetylene, trifluoroethylene, pentafluoroethane (R-125), 1,1,1,2-tetrafluoroethane (R-134a), (Z)-1,2-difluoroethylene, tetrafluoroethylene, and cis- and trans-1H-nonafluoro-2-propoxyethene.

Embodiments of the present disclosure are described above; however, the present disclosure is not limited to these examples. Of course, the present disclosure can be carried out in various forms without departing from the gist thereof.

As described above, the present disclosure includes the following.

1. A method for purifying a phosphorus-containing olefin compound salt, comprising reprecipitating and/or recrystallizing a solid comprising at least one phosphorus-containing olefin compound salt selected from the group consisting of:

a phosphorus-containing olefin compound salt A represented by the following formula (1):

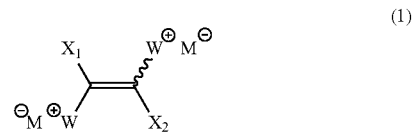

(1)

wherein $X_1$ and $X_2$ are each independently F, Cl, Br, I, or H; $W^+$s are the same or different and each is a monovalent cation comprising $PR_3$ or $P(OR)_3$, provided that Rs are groups having a saturated or unsaturated structure containing C and H, are optionally bonded together to form a ring, and optionally contain an atom other than C and H; three Rs included in $R_3$ and $(OR)_3$ are optionally the same or different; and $M^-$ is a monovalent anion comprising an atom or a compound; and a phosphorus-containing olefin compound salt B represented by the following formula (2):

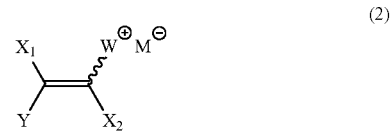

(2)

wherein $X_1$, $X_2$, $W^+$, and $M^-$ are as defined above, and Y is F, Cl, Br, I, H, an alkyl group, an alkyl ether group, a fluoroalkyl group, or a fluoroalkyl ether group;

in a solvent, thereby obtaining a purified product of the phosphorus-containing olefin compound salt.

2. The purification method according to Item 1, wherein the solvent is at least one member selected from the group consisting of ethyl acetate, n-propyl acetate, isopropyl acetate, n-butyl acetate, methanol, ethanol, propanol, isopropanol, and butanol.

3. The purification method according to Item 1 or 2, wherein after the solid is dissolved in a solvent at 45 to 60° C., the temperature of a solution is reduced at −0.25° C./rain or less to thereby perform reprecipitation and/or recrystallization.

4. The purification method according to any one of Items 1 to 3, further comprising extracting the purified product by suction filtration and/or pressure filtration.

5. The purification method according to any one of Items 1 to 4, wherein the solid comprises at least one compound selected from the group consisting of:
(trans-2-perfluoropropoxy-1,2-difluoroethen-1-yl) (tributyl) phosphonium tetrafluoroboranuide, (cis-2-perfluoropropoxy-1,2-difluoroethen-1-yl)(tributyl) phosphonium tetrafluoroboranuide,
perfluoropropoxy vinyl ether,
(2,2,3,3,3-pentafluoro-1-tributylphosphin-1-one) tetrafluoroboranuide,
boron trifluoride tributylphosphine oxide,
tetrafluoroboric acid,
(1,2-difluoroethen-1-yl) (tributyl) phosphonium tetrafluoroboranuide),
diethyl ether,
dimethyl ether, and
2-methoxy-2-methylpropane.

6. The purification method according to any one of Items 1 to 5, wherein the purity of the phosphorus-containing olefin compound salt in the purified product is 95 mass % or more.

7. A method for producing an olefin compound, comprising reacting the purified product obtained by the purification method according to any one of Items 1 to 6 and a base to thereby obtain a reaction product containing a dephosphorized and hydrogenated olefin compound.

8. The production method according to Item 7, wherein the olefin compound is (E)-1,2-difluoroethylene.

9. The production method according to Item 7 or 8, wherein the reaction product comprises (E)-1,2-difluoroethylene and at least one member selected from the group consisting of acetylene, trifluoroethylene, pentafluoroethane (R-125), 1,1,1,2-tetrafluoroethane (R-134a), (Z)-1,2-difluoroethylene, tetrafluoroethylene, and cis- and trans-1H-nonafluoro-2-propoxyethene.

10. A solid comprising at least one phosphorus-containing olefin compound salt selected from the group consisting of:
a phosphorus-containing olefin compound salt A represented by the following formula (1):

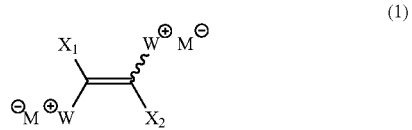

wherein $X_1$ and $X_2$ are each independently F, Cl, Br, I, or H; $W^+$s are the same or different and each is a monovalent cation comprising $PR_3$ or $P(OR)_3$, provided that Rs are groups having a saturated or unsaturated structure containing C and H, are optionally bonded together to form a ring, and optionally contain an atom other than C and H; three Rs included in $R_3$ and $(OR)_3$ are optionally the same or different; and $M^-$ is a monovalent anion comprising an atom or a compound; and
a phosphorus-containing olefin compound salt B represented by the following formula (2):

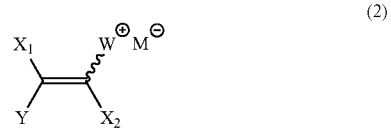

wherein $X_1$, $X_2$, $W^+$, and $M^-$ are as defined above, and Y is F, Cl, Br, I, H, an alkyl group, an alkyl ether group, a fluoroalkyl group, or a fluoroalkyl ether group;
and further comprising at least one compound selected from the group consisting of:
(trans-2-perfluoropropoxy-1,2-difluoroethen-1-yl) (tributyl) phosphonium tetrafluoroboranuide,
(cis-2-perfluoropropoxy-1,2-difluoroethen-1-yl) (tributyl) phosphonium tetrafluoroboranuide,
perfluoropropoxy vinyl ether,
(2,2,3,3,3-pentafluoro-1-tributylphosphin-1-one) tetrafluoroboranuide,
boron trifluoride tributylphosphine oxide,
tetrafluoroboric acid,
(1,2-difluoroethen-1-yl) (tributyl) phosphonium tetrafluoroboranuide),
diethyl ether,
dimethyl ether, and
2-methoxy-2-methylpropane.

EXAMPLES

Embodiments of the present disclosure are described in more detail below based on Examples. However, the present disclosure is not limited to the scope of the Examples.

Example 1

A target olefin compound (C) (R1132(E)) was synthesized from a raw material olefin (A) ($C_3F_7OCF=CF_2$) according to the following formula:

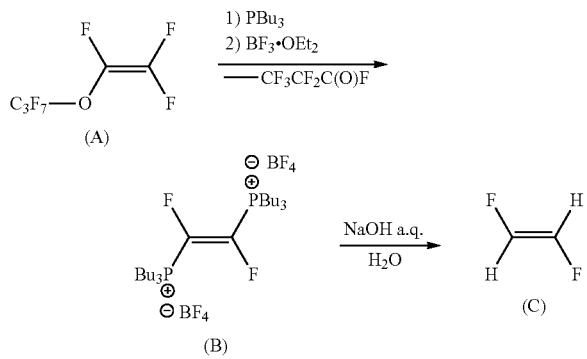

Specifically, $PBu_3$ (89.2 g, 440 mmol) was dissolved in ether (500 ml) at 5° C. While stirring this solution, the raw material olefin (A) (39.2 g, 147 mmol) was added dropwise at a temperature of 5° C. over 20 minutes to cause reaction.

After the reaction mixture was maintained at 5° C. for 2 hours, $BF_3OEt_2$ (63.3 g, 446 mmol) was added at a temperature of 5 to 20° C., and the mixture was then stirred at a temperature of 25° C. for 1.5 hours.

The upper ether layer was decanted, and the residue was washed with ether and dried in vacuum, thereby obtaining a white sticky substance (a solid containing the phosphorus-containing olefin compound salt (B)) (155.5 g). When the solid was analyzed by NMR, 16 mass % of $[CF_3CF_2C(O)—PBu_3][BF_4]$ was contained as an impurity.

The solid containing the phosphorus-containing olefin compound salt (B) was dissolved in ethyl acetate at 50° C., and the temperature of the solution was reduced at −0.25° C./min to perform reprecipitation and/or recrystallization, thereby obtaining a purified product. The purified product was extracted by suction filtration.

A 50 mass % aqueous sodium hydroxide solution was added to the purified product to react with a base. The liquid temperature was raised from 28° C. to 50° C.

The reaction product (distillate) with the base was analyzed by gas chromatogram.

The results are shown in Table 1 below.

Comparative Example 1

A target olefin compound (C) (R1132(E)) was synthesized from a raw material olefin (A) ($C_3F_7OCF=CF_2$) under the same conditions as in Example 1, except that the solid containing the phosphorus-containing olefin compound salt (B) was not reprecipitated and recrystallized. That is, a white sticky substance (a solid containing the phosphorus-containing olefin compound salt (B)) was directly reacted with a base.

The results are shown in Table 1 below.

TABLE 1

| | Gas chromatogram analysis results of reaction product (distillate) with base (GC %) | | | | | | | | |
|---|---|---|---|---|---|---|---|---|---|
| | HC≡CH | $CF_2$=CFH | R1132(E) | R-125 | R1132(Z) | R-134a | cis-$C_3H_7OCF$=CFH | cis-$C_3H_7OCF$=CFH | Total |
| Comparative Example 1 | 1.041 | 8.95 | 82.911 | 0.604 | 1.665 | 1.278 | 0.225 | 0.322 | 96.996 |
| Example 1 | 0.167 | 0.689 | 98.611 | 0.02 | n.d. | 0.256 | n.d. | n.d. | 99.743 |

As is clear from the results of Table 1, in the case of Example 1, in which the phosphorus-containing olefin compound salt (B) was purified by reprecipitation and/or recrystallization, the yield of the target olefin compound (C) (R1132(E)) was higher, and the content of isomers and other by-products was relatively lower, compared with Comparative Example 1, in which reprecipitation and/or recrystallization was not performed.

The invention claimed is:
1. A method for purifying a phosphorus-containing olefin compound salt, comprising reprecipitating and/or recrystallizing a solid comprising at least one phosphorus-containing olefin compound salt selected from the group consisting of:
a phosphorus-containing olefin compound salt A represented by the following formula (1):

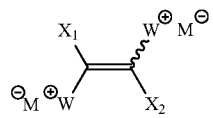

(1)

wherein $X_1$ and $X_2$ are each independently F, Cl, Br, I, or H; each $W^+$ is the same or different and is a monovalent cation comprising $PR_3$ or $P(OR)_3$, provided that each R is independently a group having a saturated or unsaturated structure containing C and H, each R is optionally bonded together to form a ring, and each R optionally contains an atom other than C and H; and $M^-$ is a monovalent anion comprising an atom or a compound; and
a phosphorus-containing olefin compound salt B represented by the following formula (2):

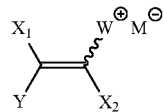

(2)

wherein $X_1$, $X_2$, $W^+$, and $M^-$ are as defined above, and Y is F, Cl, Br, I, H, an alkyl group, an alkyl ether group, a fluoroalkyl group, or a fluoroalkyl ether group;
in a solvent, thereby obtaining a purified product of the phosphorus-containing olefin compound salt in a solution,
wherein after the solid is dissolved in the solvent at 45 to 60° C., the temperature of the solution is reduced at −0.25° C./min or less to thereby perform the reprecipitation and/or recrystallization.

2. The method according to claim 1, wherein the solvent is at least one selected from the group consisting of ethyl acetate, n-propyl acetate, isopropyl acetate, n-butyl acetate, methanol, ethanol, propanol, isopropanol, and butanol.

3. The method according to claim 1, further comprising extracting the purified product by suction filtration and/or pressure filtration.

4. The method according to claim 1, wherein the solid comprises at least one compound selected from the group consisting of:
(trans-2-perfluoropropoxy-1,2-difluoroethen-1-yl) (tributyl) phosphonium tetrafluoroboranuide,
(cis-2-perfluoropropoxy-1,2-difluoroethen-1-yl) (tributyl) phosphonium tetrafluoroboranuide,
perfluoropropoxy vinyl ether,
(2,2,3,3,3-pentafluoro-1-tributylphosphin-1-one) tetrafluoroboranuide,
boron trifluoride tributylphosphine oxide,
tetrafluoroboric acid,
(1,2-difluoroethen-1-yl) (tributyl) phosphonium tetrafluoroboranuide),
diethyl ether,
dimethyl ether, and
2-methoxy-2-methylpropane.

5. The method according to claim 1, wherein the purity of the phosphorus-containing olefin compound salt in the purified product is 95 mass % or more.

6. A method for producing an olefin compound, comprising reacting the purified product obtained by the method according to claim 1 and a base to thereby obtain a reaction product containing a dephosphorized and hydrogenated olefin compound.

7. The method according to claim 6, wherein the olefin compound is (E)-1,2-difluoroethylene.

8. The method according to claim 6, wherein the reaction product comprises (E)-1,2-difluoroethylene and at least one compound selected from the group consisting of acetylene, trifluoroethylene, pentafluoroethane, 1,1,1,2-tetrafluoroethane, (Z)-1,2-difluoroethylene, tetrafluoroethylene, and cis-1H-nonafluoro-2-propoxyethene, and trans-1H-nonafluoro-2-propoxyethene.

9. A solid comprising:
(i) at least one phosphorus-containing olefin compound salt selected from the group consisting of:
a phosphorus-containing olefin compound salt A represented by the following formula (1):

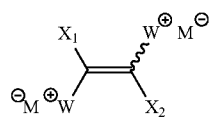
(1)

wherein $X_1$ and $X_2$ each independently F, Cl, Br, I, or H; each $W^+$ is the same or different and is a monovalent cation comprising $PR_3$ or $P(OR)_3$, provided that each R is independently a group having a saturated or unsaturated structure containing C and H, each R is optionally bonded together to form a ring, and each R optionally contains an atom other than C and H; and $M^-$ is a monovalent anion comprising an atom or a compound; and a phosphorus-containing olefin compound salt B represented by the following formula (2):

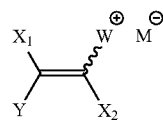
(2)

wherein $X_1$, $X_2$, $W^+$, and $M^-$ are as defined above, and Y is F, Cl, Br, I, H, an alkyl group, an alkyl ether group, a fluoroalkyl group, or a fluoroalkyl ether group; and (ii) at least one compound selected from the group consisting of:
(trans-2-perfluoropropoxy-1,2-difluoroethen-1-yl) (tributyl) phosphonium tetrafluoroboranuide,
(cis-2-perfluoropropoxy-1,2-difluoroethen-1-yl) (tributyl) phosphonium tetrafluoroboranuide,
perfluoropropoxy vinyl ether,
(2,2,3,3,3-pentafluoro-1-tributylphosphin-1-one) tetrafluoroboranuide,
boron trifluoride tributylphosphine oxide,
tetrafluoroboric acid,
(1,2-difluoroethen-1-yl) (tributyl) phosphonium tetrafluoroboranuide),
dimethyl ether, and
2-methoxy-2-methylpropane.

\* \* \* \* \*